United States Patent
Nakamura et al.

(10) Patent No.: US 10,680,454 B2
(45) Date of Patent: Jun. 9, 2020

(54) POWER SUPPLY CIRCUIT FOR BIOLOGICAL SIGNAL MEASUREMENT CIRCUIT AND BIOLOGICAL SIGNAL MEASURING APPARATUS

(71) Applicant: SIMPLEX QUANTUM INC., Tokyo (JP)

(72) Inventors: Hiroshi Nakamura, Tokyo (JP); Yuji Hamada, Tokyo (JP)

(73) Assignee: Simplex Quantum Inc., Tokyo (JP)

( * ) Notice: Subject to any disclaimer, the term of this patent is extended or adjusted under 35 U.S.C. 154(b) by 185 days.

(21) Appl. No.: 15/996,807

(22) Filed: Jun. 4, 2018

(65) Prior Publication Data

US 2019/0372379 A1  Dec. 5, 2019

(51) Int. Cl.
*H02J 7/00* (2006.01)
*A61B 5/0408* (2006.01)
*H02J 7/34* (2006.01)

(52) U.S. Cl.
CPC .......... *H02J 7/0068* (2013.01); *A61B 5/0408* (2013.01); *H02J 7/0047* (2013.01);
(Continued)

(58) Field of Classification Search
CPC ...... H02J 7/0013; H02J 7/0032; H02J 7/0047; H02J 7/0049; H02J 7/005; H02J 7/0068;
(Continued)

(56) References Cited

U.S. PATENT DOCUMENTS

| 4,096,866 A | * | 6/1978 | Fischell | ................. A61N 1/378 607/34 |
| 6,226,539 B1 | * | 5/2001 | Potratz | ............... A61B 5/14551 356/41 |

(Continued)

FOREIGN PATENT DOCUMENTS

| JP | 07087687 A | 3/1995 |
| JP | 08130833 A | 5/1996 |

(Continued)

OTHER PUBLICATIONS

Office action issued in corresponding Japanese Patent App. No. 2017-041264, dated May 21, 2019 (with translation).

(Continued)

*Primary Examiner* — Carl H Layno
*Assistant Examiner* — Jane C Kalinock
(74) *Attorney, Agent, or Firm* — Greer Burns & Crain Ltd.

(57) ABSTRACT

Provided is a power supply circuit that supplies electric power to a biological signal measurement circuit configured to detect, with an electrode set in contact with a human body, a biological signal which is a weak electric signal emitted by the human body. The power supply circuit includes a capacitance element accumulating the electric power, and a circuit switch coupled between the capacitance element and an external power supply for supplying electric power to the capacitance element, and configured to switch, not through a state where the external power supply and the biological (Continued)

signal measurement circuit are electrically coupled, a first state where the capacitance element establishes electrical continuity with the external power supply and is enabled to be charged, and a second state where the capacitance element establishes electrical continuity with the biological signal measurement circuit and is enabled to supply power to the biological signal measurement circuit.

7 Claims, 7 Drawing Sheets

(52) U.S. Cl.
CPC ..... *A61B 2560/0214* (2013.01); *H02J 7/0049* (2020.01); *H02J 7/345* (2013.01)

(58) Field of Classification Search
CPC ......... H02J 7/02; H02J 7/345; A61B 5/04021; A61B 5/0404; A61B 5/04284; A61B 5/04288; H01G 9/016
USPC .......................................................... 607/34
See application file for complete search history.

(56) References Cited

U.S. PATENT DOCUMENTS

| | | | | |
|---|---|---|---|---|
| 2004/0045801 | A1* | 3/2004 | Shimizu | H01H 9/38 200/547 |
| 2006/0208789 | A1* | 9/2006 | Shimada | H02M 3/157 327/540 |
| 2006/0239040 | A1* | 10/2006 | Fukumoto | H02M 3/33507 363/21.01 |
| 2013/0096539 | A1* | 4/2013 | Wood | H02J 7/0027 606/1 |

FOREIGN PATENT DOCUMENTS

| | | |
|---|---|---|
| JP | 2005312104 A | 11/2005 |
| JP | 2008306788 A | 12/2008 |

OTHER PUBLICATIONS

Tomoaki Ueda, "Learn from an Electrocardiogram! Point of Medical/Healthcare Apparatus Manufacturing", Interface, Cq Publishing Co_, Ltd., pp. 114-126, Jan. 2013 (with English language abstract) X.

\* cited by examiner

POWER SUPPLY CIRCUIT FOR BIOLOGICAL SIGNAL MEASUREMENT CIRCUIT AND BIOLOGICAL SIGNAL MEASURING APPARATUS

BACKGROUND

Technical Field

The present invention relates to a power supply circuit for a biological signal measurement circuit and a biological signal measuring apparatus.

Related Art

Electrocardiogram (ECG), electromyogram (EMG), and electroencephalogram (EEG) are well known as biological signals, which are electric signals obtained from an organism. Those electric signals are extremely weak. Usually, the electric signals are measured with multiple electrodes set in direct contact with a human body.

Large measuring apparatuses for medical tests have been present. However, with recent advancement in a size reduction and power saving of the measuring apparatuses, battery-driven small portable terminals have been also used to measure biological signals conveniently. These small portable terminals mainly use a rechargeable secondary battery as a power supply and wireless transmission such as Bluetooth (registered trademark) as data transmitting means.

In addition to electric signal measurement of electrocardiogram, electromyogram, and electroencephalogram, some of the small portable terminals perform measurement of movements of a human body such as acceleration and angular velocity, measurement of movements and characteristics of blood vessels using light and radio waves, measurement of a skin temperature, and the like. All the small portable terminals have high commonality in terms of driving by the secondary battery and data transmission by radio.

By measuring these electric signals concerning the biological information, that is, biological signals and performing data processing of the biological signals, useful information concerning the human body more closely related to life such as a blood pressure, a stress degree, an energy consumption amount, and a sleeping time is also obtained. Further, such measurement is applied to individual authentication.

As to the convenient biological signal measurement having a wide range of uses, there is a demand for a stationary small terminal in addition to a small portable terminal of a type always worn on the body. Such a stationary small terminal is expected to achieve theft and loss prevention, long life, unnecessity of maintenance, and the like. As technical information concerning measurement of biological signals, for example, a conventional hardware configuration of a general electrocardiograph is described in Tomoaki Ueda, "Learn from an Electrocardiogram! Point of Medical/Healthcare Apparatus Manufacturing", Interface, CQ Publishing Co., Ltd., January 2013, pp. 114 to 126 (hereinafter referred to as "Ueda").

In general, the stationary small terminal is supplied with electric power from an external apparatus such as a computer, and performs data transmission by wire rather than by radio. Specifically, for both of the data transmission and the power supply, a USB interface is often used to couple the small terminal to the external apparatus. As described in Ueda, the electrocardiograph itself is a technically established measuring apparatus. However, there are not a few technical problems that should be solved in configuring the electrocardiograph as a portable terminal or a stationary small terminal.

One of the technical problems is prevention of an electric shock of a person as a measurement target of biological signals. An electrode of the apparatus needs to be brought into direct contact with a human body to measure biological signals. A measurement circuit of the apparatus needs to be completely electrically insulated from an external apparatus on a power supply side in order to prevent an electric shock of a measurement target person. This electric insulation is established by using means for supplying electric power from a power supply circuit of the external apparatus to a measuring apparatus via an isolation transformer. However, to transmit the electric power via the transformer, it is necessary to convert a direct current on a primary side into a high-frequency alternating current, which incurs a lot of induction noise in the conversion process. An apparatus that treats weak signals such as biological signals also requires a power supply circuit to achieve super low noise. Therefore, use of the insulated transformer is undesirable. The insulated transformer is an expensive component and needs the power conversion circuit described above. Therefore, the insulated transformer prevents a reduction in the cost of the apparatus.

The stationary small measuring apparatus is requested to be usable without necessity of maintenance for a long period. However, when a general secondary battery is used as a power supply of the measuring apparatus, the measuring apparatus has problems in that the apparatus cannot be used during a charging period, and it is difficult to make maintenance unnecessary for a long period due to the limitation of the number of times of charging of the secondary battery.

SUMMARY

The present invention has been made to solve the above and other problems, and an object of the present invention is to provide a power supply circuit for a biological signal measurement circuit and a biological signal measuring apparatus that enable a measurement system and a power supply system to be electrically insulated from each other with a simple configuration, and that can improve convenience by greatly reducing a charging time.

An aspect of the present invention for achieving the above and other objects is a power supply circuit for supplying electric power to a biological signal measurement circuit configured to detect, with an electrode set in contact with a human body, a biological signal, which is a weak electric signal emitted by the human body. The power supply circuit includes: a capacitance element that accumulates the electric power; and a circuit switch that is coupled between the capacitance element and an external power supply for supplying electric power to the capacitance element, and that is configured to switch, not through a state where the external power supply and the biological signal measurement circuit are electrically coupled, a first state where the capacitance element is made to establish electrical continuity with the external power supply and is enabled to be charged, and a second state where the capacitance element is made to establish electrical continuity with the biological signal measurement circuit and is enabled to supply power to the biological signal measurement circuit.

The circuit switch can be configured to usually retain the second state and come into the first state only for a period in which a command from an outside is given.

The circuit switch can be a two-circuit two-contact push button switch of a momentary type.

An electric double layer capacitor can be used as the capacitance element.

In addition, the power supply circuit may further include a current detection circuit provided on an external power supply side of the circuit switch, the current detection circuit including a comparator, a voltage dividing resistor, a current detection resistor, and a light emitting diode. Then, the power supply circuit may light up or extinguish the light emitting diode to perform a notification that the charging to the capacitance element is completed.

Meanwhile, the power supply circuit may further include a voltage smoothing circuit provided on a biological signal measurement circuit side of the circuit switch, the voltage smoothing circuit including a comparator, a voltage dividing resistor, a reference voltage source, and a voltage regulator with an enable terminal. When an inter-terminal voltage of the capacitance element is equal to or lower than a minimum operation voltage of the biological signal measurement circuit, the power supply circuit may stop the power supply to the biological signal measurement circuit to prevent a decrease in electric charges of the capacitance element.

Another aspect of the present invention is a biological signal measuring apparatus including the power supply circuit having the configuration explained above.

According to the present invention, provided are a power supply circuit and a biological signal measuring apparatus that enable a measurement system and a power supply system to be electrically insulated from each other with a simple configuration, and that can improve convenience by greatly reducing a charging time.

DETAILED DESCRIPTION OF THE EMBODIMENTS

Figure 1:
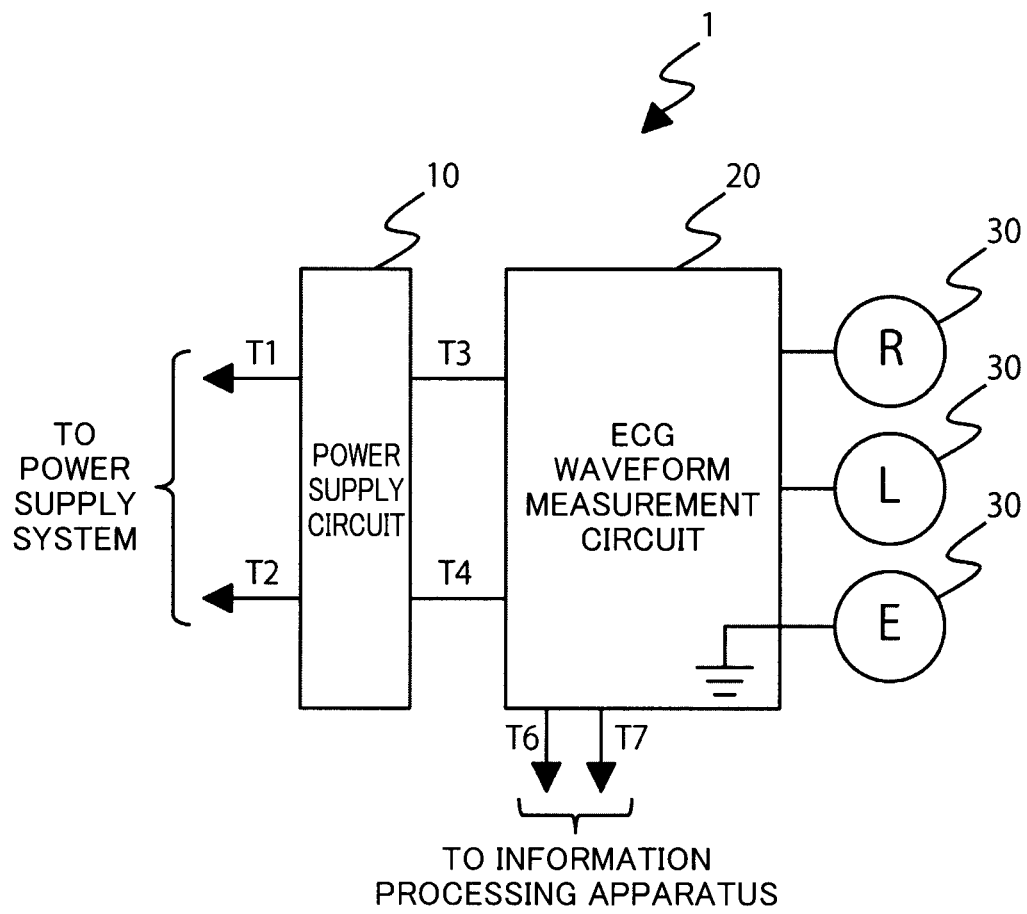
FIG. 1 is a schematic block diagram of an electrocardiographic waveform measuring apparatus according to an embodiment of the present invention.

In describing embodiments illustrated in the drawings, specific terminology is employed for the sake of clarity. However, the disclosure of the present specification is not intended to be limited to the specific terminology so selected and it is to be understood that each specific element includes all technical equivalents that have a similar function, operate in a similar manner, and achieve a similar result.

As used herein, the singular forms "a", "an", and "the" are intended to include the plural forms as well, unless the context clearly indicates otherwise.

Referring to the drawings, wherein like reference numerals designate identical or corresponding parts throughout the several views, embodiments of the present disclosure are described below.

In FIG. 1, a schematic configuration example of an electrocardiographic waveform measuring apparatus according to the embodiment of the present invention is schematically shown. The present invention can be applied to a circuit that measures various biological signals such as electrocardiogram, electromyogram, and electroencephalogram. As to this embodiment, application to an electrocardiographic waveform measuring apparatus 1 is explained.

As shown in FIG. 1, an electrocardiographic waveform measuring apparatus 1 in this embodiment includes a power supply circuit 10, an electrocardiographic waveform measurement circuit 20, and electrodes 30. The power supply circuit 10 includes a large-capacity capacitance element, for example, an electric double layer capacitor. The power supply circuit 10 is configured to be chargeable from a power supply device of an external information processing apparatus such as a personal computer (PC) or an independent external power supply apparatus via lead wires T1 and T2. The capacitance element of the power supply circuit 10 can supply electric power to the electrocardiographic waveform measurement circuit 20 via lead wires T3 and T4. A configuration example of the power supply circuit 10 is explained below.

The electrocardiographic waveform measurement circuit 20 has a function of performing processing such as amplification, waveform shaping, noise removal, and analog/digital conversion (AD conversion) concerning a weak electrocardiographic signal received from the electrodes 30 and delivering the electrocardiographic signal to the information processing apparatus such as a PC via lead wires T6 and T7 as an electrocardiographic digital signal. Note that it is desirable for safety of a human body, which is a measurement target by the electrocardiographic waveform measurement circuit 20, to provide circuit devices for electric insulation such as photocouplers in the lead wires T6 and T7 between the electrocardiographic waveform measurement circuit 20 and the external information processing apparatus. The electrocardiographic digital signal can be transmitted in various signal systems such as USB, UART, I2C, and SPI. Note that the electrocardiographic digital signal can also be transmitted from the electrocardiographic waveform measurement circuit 20 to the external information processing apparatus by wireless communication such as Bluetooth™. Various specific configuration examples of the electrocardiographic waveform measurement circuit 20 are disclosed in publicly-known technical documents such as Ueda. Therefore, explanation of the specific configuration examples is omitted.

The electrodes 30 are conductive members brought into contact with the human body, which is the measurement target, to pick up an electrocardiographic signal. At least a pair of electrodes are set in positions across the heart to detect an electrocardiographic signal as a voltage change between the electrodes.

Figure 2:
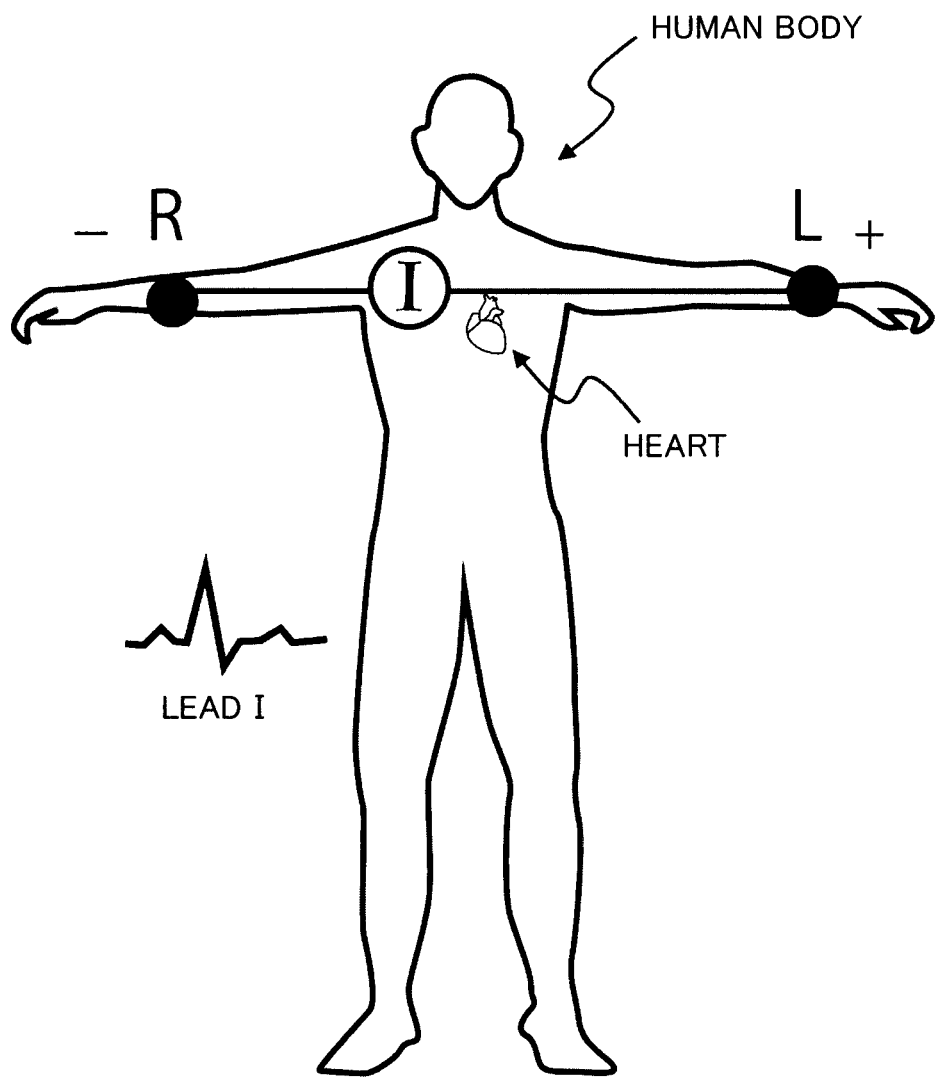
FIG. 2 is a diagram for explaining LEAD I of an electrocardiographic waveform.

In FIG. 2, an explanatory diagram of a measurement example of an electrocardiographic waveform is shown. A method of disposing a pair of electrodes R and L on the left and right hands or wrists to measure an electrocardiographic signal is often used as a simple measurement method. The electrocardiographic signal obtained by such a measurement method is called LEAD I.

In a full-scale electrocardiographic signal acquisition in a medical facility, a method called LEAD XII induction method for disposing thirteen electrodes on a body surface is used. In this case, a ground electrode is usually attached to a right ankle most distant from the heart. By using the ground electrode, alternating-current noise of 50 Hz or 60 Hz induced in the entire body deriving from a commercial power supply can be greatly reduced to contribute to improve measurement accuracy.

However, in LEAD I measurement using both the hands, it is ideal to attach the ground electrode in a place other than both the hands. However, practically, it is difficult to provide the ground electrode in a place other than a finger or a wrist.

Therefore, in this embodiment, concerning three electrodes 30 shown in FIG. 1, one hand touches one electrode 30(L) with one finger and the other hand touches the remaining two electrodes 30(R) and 30(E) using two fingers. One electrode 30(E) of the two electrodes 30(R) and 30(E) is configured as a ground electrode. By configuring the electrodes 30 in this way, it was confirmed that a reduction effect of noise by addition of the ground electrode surpasses an adverse effect of attenuation of an electrocardiographic signal by the near ground electrode and, as a result, a satisfactory electrocardiographic signal is obtained.

Figure 3:
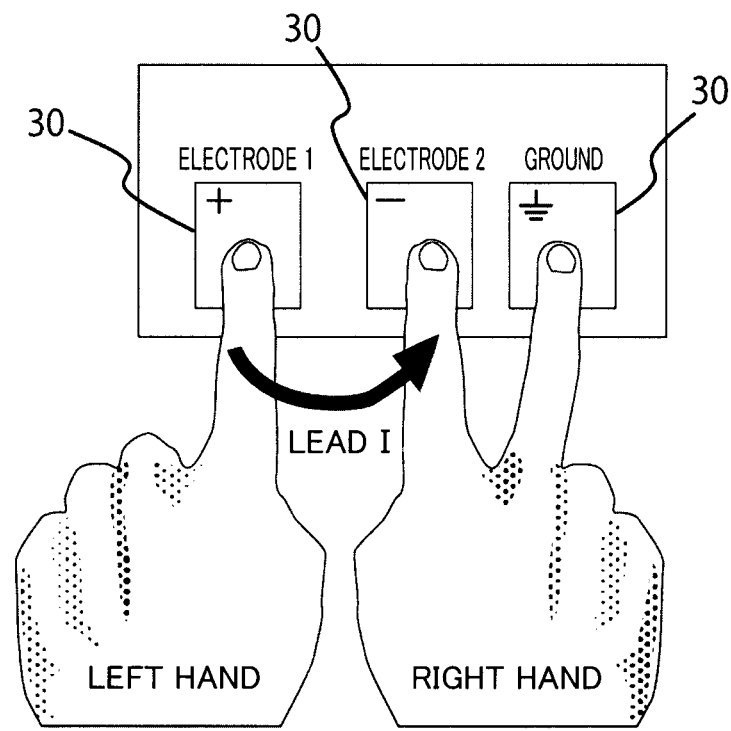
FIG. 3 is a schematic diagram showing a configuration example of an electrode.

A specific disposition example of the electrodes 30 is shown in FIG. 3. In FIG. 3, the three electrodes 30 shown in FIG. 1 are disposed such that the left hand index finger can touch an electrode 1, the right hand index finger can touch an electrode 2, and the right hand middle finger can touch a ground electrode. In this case, to detect an electrocardiographic signal of the LEAD I, the electrode 1 and the electrode 2 shown in FIG. 3 are respectively touched by fingers of the different left and right hands such that the electrode 1 and the electrode 2 are disposed across the heart as shown in FIG. 2. The hands touching the electrode 1 and the electrode 2 may be changed as long as the electrode 1 and the electrode 2 are touched by different hands. The three electrodes 30 may be modularized as one electrode unit or may be disposed, considering convenience and the like of a user, in an appropriate position of another apparatus in which the electrocardiographic waveform measurement circuit 20 shown in FIG. 1 is provided, for example, a terminal apparatus that uses an electrocardiographic waveform for individual authentication.

Note that the ground electrode is provided in the configuration example of the electrodes 30 explained above. However, instead, there is also a method of actively applying a signal to a third electrode to cancel noise using an electrode called Driven Right Leg (DRL) electrode. In this case, the user touches the DRL electrode rather than the ground electrode with a third finger.

The power supply circuit 10 shown in FIG. 1 is explained. In the power supply circuit 10 in this embodiment, a large-capacity electric double layer capacitor having a capacity of 10 mF or more is adopted as a capacitance element. The capacitor is quickly charged from an external power supply using a DPDT push button switch of a momentary type and electric charges accumulated in the capacitor are gently discharged to supply necessary electric power to the electrocardiographic waveform measurement circuit 20. The DPDT form is adopted as the switch to collectively switch not only a power supply line between the external power supply and the capacitor but also a ground line.

By using the DPDT push button switch of the momentary type, the capacitor is quickly charged only while the switch is pressed. Both of the power supply line and the ground line are not in a state where the power supply line and the ground line simultaneously electrically couple the external power supply and the electrocardiographic waveform measurement circuit 20. That is, because the electrocardiographic waveform measurement circuit 20 is electrically completely insulated from a power supply system such as the external power supply, the human body, which is the measurement target of the electrocardiographic waveform measurement circuit 20, is also electrically completely insulated from the external power supply. There is no concern about an electric shock and the like. Because the electric power stored in the capacitor is used, a power supply of the electrocardiographic waveform measurement circuit 20 has super low noise. Further, unlike various secondary batteries, the capacitor has almost no limitation on the number of times of charging. Therefore, the capacitor can be substantially free from maintenance.

Figure 4:
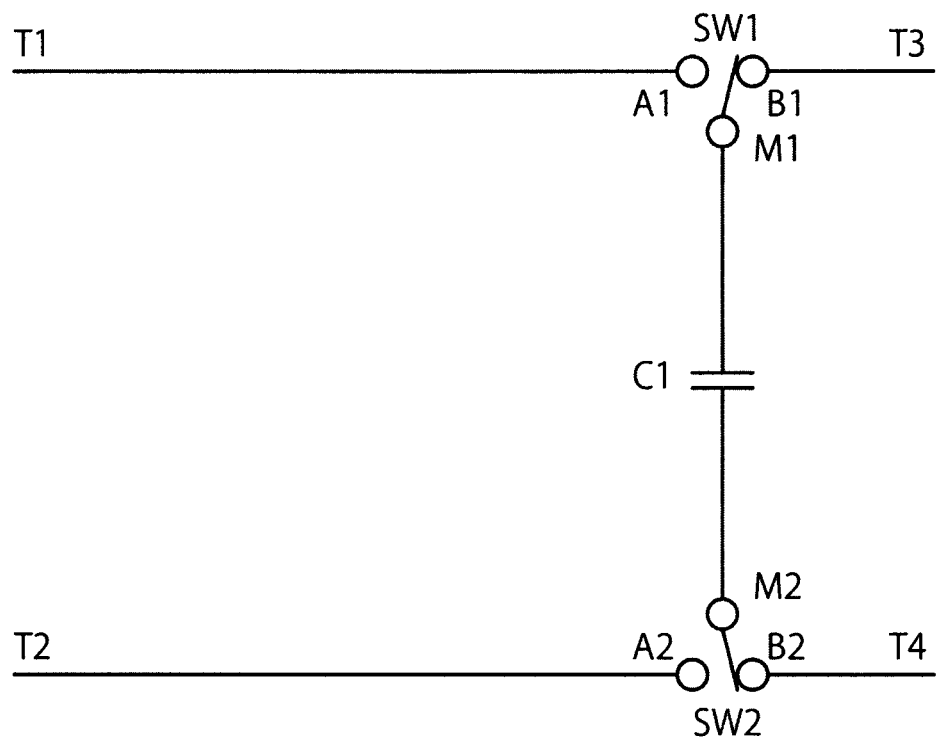
FIG. 4 is a schematic circuit diagram showing an example of a power supply circuit in the embodiment.

Referring to FIG. 4, in the power supply circuit 10, the lead wires T1 (the power supply line) and T2 (the ground line) coupled to the external power supply and the lead wires T3 (the power supply line) and T4 (the ground line) coupled to the electrocardiographic waveform measurement circuit 20 are respectively insulated at contacts A1, B1, A2, and B2. The contacts are configured to be opened and closed by a two-circuit two-contact (hereinafter abbreviated as "DPDT") push button switch (circuit switch) including switches SW1 and SW2 that operate in conjunction with each other. The switches SW1 and SW2 are usually coupled to the contacts B1 and B2, so that both terminals of a large-capacity capacitor C1 coupled between common terminals M1 and M2 of the switches SW1 and SW2 are coupled to the lead wires T3 and T4 (a second state). Both the terminals of the capacitor C1 are coupled to the contacts A1 and A2 only while the push button is being pressed (a first state). Such an operation is called momentary operation. A switch that realizes the momentary operation is easily available in the market. With the action of the switches SW1 and SW2, the contacts A1 and B1 or the contacts A2 and B2 do not come into contact at all during the operation.

As explained above, the large-capacity capacitor C1 is coupled between the common terminals M1 and M2 of the switches SW1 and SW2. A large capacity is requested for the capacitor C1. Therefore, it is suitable to use an electric double layer capacitor or a lithium ion capacitor. However, the capacitor C1 is not limited to the capacitors.

Figure 5:
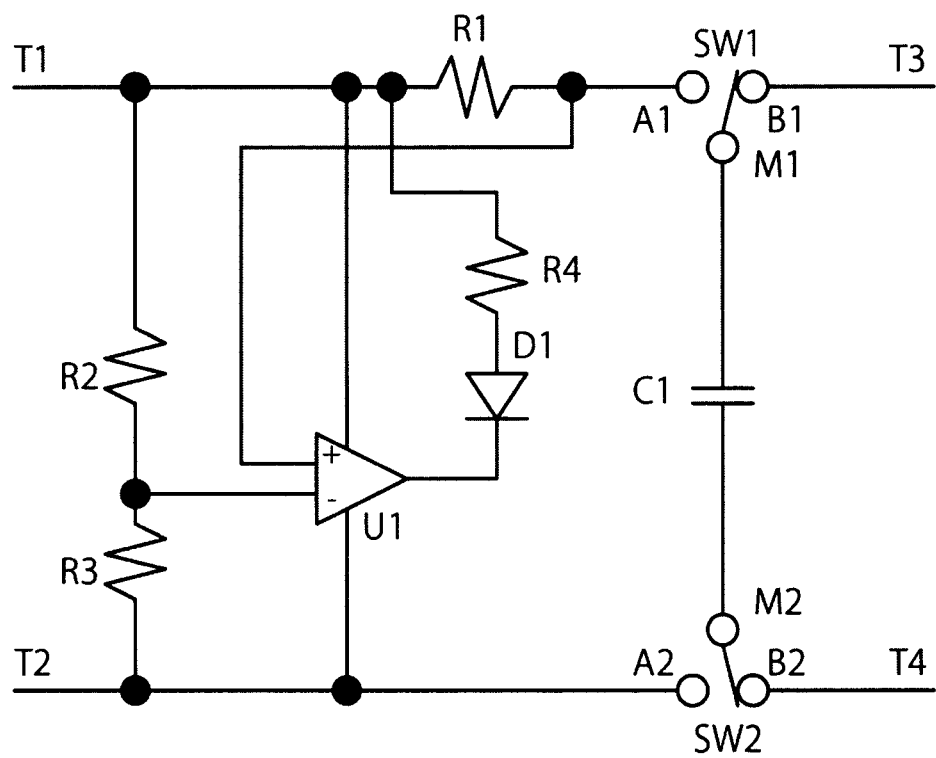
FIG. 5 is a diagram showing a modification on an external power supply side of the power supply circuit shown in FIG. 4.

A modification of the circuit shown in FIG. 4 is explained. In this modification, as shown in FIG. 5, a circuit for detecting that sufficient electric charges are charged in the capacitor C1 is added. A charging current is limited because internal resistance having a certain degree of a value is present in the large-capacity capacitor C1. An excessively large current that may cause overheat or the like usually does not flow to a power supply system side. However, when a value of the internal resistance of the capacitor C1 is small and a peak charging current exceeds an allowable current value of the power supply system, a resistor for current limitation can be added to the capacitor C1 in series.

Figure 6:
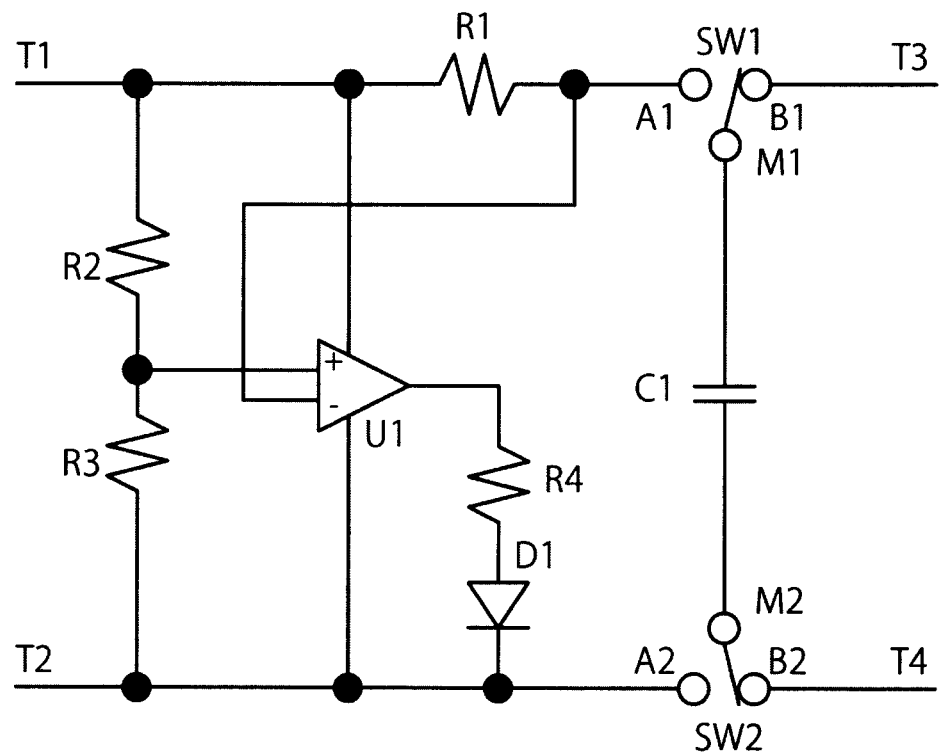
FIG. 6 is a diagram showing a modification of the power supply circuit shown in FIG. 5.

In FIG. 5, U1 is a comparator operable rail-to-rail. Electric power of the comparator is supplied from the lead wires T1 and T2 on the power supply side. R1 is a resistor having a small value (e.g., 1Ω) for current detection, R2 and R3 are voltage dividing resistors, D1 is a light emitting diode, and R4 is a current limitation resistor of the light emitting diode. In FIG. 5, a voltage after voltage drop in R1 is coupled to a plus terminal of the comparator U1, a voltage divided by R2 and R3 is coupled to a minus terminal of the comparator U1, and a series circuit of D1 and R4 is coupled between an output of U1 and the lead wire T1. On the other hand, a configuration equivalent to FIG. 5 is obtained when, as shown in FIG. 6, the voltage after voltage drop in R1 is coupled to the minus terminal of the comparator U1, the voltage divided by R2 and R3 is coupled to the plus terminal of the comparator U1, and the series circuit of D1 and R4 is coupled between the output of the comparator U1 and the lead wire T2.

The operation of the circuit illustrated in FIG. 5 is explained. When the push button is pressed to operate SW1 and SW2, both the positive and negative electrodes of the capacitor C1 are coupled to the power supply side by the switches SW1 and SW2 via the lead wires T1 and T2. An electric current flows into the capacitor C1 via the resistor for current detection R1. A charging current value in this case is limited by internal resistance of the capacitor C1. Therefore, the charging current value does not become excessively large. However, if the charging current value is excessively large, the charging current value can be limited by increasing a value of the resistor for current detection R1.

The comparator U1 compares a voltage at the contact A1 of the switch SW1, that is, a terminal voltage of the capacitor C1 and a voltage divided by the resistors R2 and R3 between the lead wires T1 and T2. When the charging current value is equal to or larger than a specified value and the potential of the plus terminal of comparator U1 is lower than the potential of the minus terminal of the comparator U1, an output of the comparator U1 is Low, an electric current flows from the lead wire T1 to the light emitting diode D1 via the resistor R4, and the light emitting diode D1 is lit. When the capacitor C1 approaches a sufficiently charged state and the potential of the plus terminal of the comparator U1 is higher than the potential of the minus terminal of the comparator U1, the output of the comparator U1 is High, the electric current does not flow to the light emitting diode D1, and the light emitting diode D1 is not lit.

That is, when the push button for operating the switches SW1 and SW2 is pressed, in the beginning, because electric charges accumulated in the capacitor C1 are little, a large charging current flows and the light emitting diode D1 is lit as explained above. As the charging of the capacitor C1 advances, when the charging current decreases to be equal to or smaller than the specified value and the output of the comparator U1 is H, the light emitting diode is extinguished. Consequently, by recognizing the extinction of the light emitting diode D1, the user can properly know that the user may release the push button because the capacitor C1 is sufficiently charged. When the user releases the push button, both the terminals of the capacitor C1 are immediately coupled to the contacts B1 and B2 on the measurement circuit side to enable measurement. Note that the operation of the circuit shown in FIG. 6 is the same as the operation of the circuit shown in FIG. 5 except that the input of the comparator U1 is reversed. Therefore, explanation of the operation is omitted. Note that, if the switches SW1 and SW2 are changed to an alternate type and are configured to be once switched to the charging state and thereafter return to the measurement circuit side with a signal indicating charging completion from the comparator U1, the user can use the electrocardiographic waveform measuring apparatus 1 without caring about whether the charging is completed.

In the above explanation, a current value for determining whether the charging of the capacitor C1 can be sufficiently performed only has to be determined according to the adopted capacitor C1 taking into account characteristics such as the internal resistance and hysteresis of the capacitor C1. The hysteresis is a phenomenon in which the voltage of the capacitor C1 decreases when the charging is suspended.

The capacitance of the capacitor C1 can be determined on the basis of an inter-terminal voltage at charging completion time, a consumed current, a minimum operation voltage, and a desired continuous measurement time of the electrocardiographic waveform measurement circuit 20, and the like. For example, if it is assumed that the inter-terminal voltage at the charging completion time is 4 V, the consumed current of the electrocardiographic waveform measurement circuit 20 is 3 mA, the minimum operation voltage is 3.1 V, and the desired continuous measurement time is 5 minutes, an appropriate capacitance of the capacitor C1 is approximately 1000 mF. Note that a withstanding voltage of the capacitor C1 can be determined on the basis of a maximum of a power supply voltage of the external power supply coupled to the capacitor C1. As the capacitor C1, one capacitance element having desired capacitance may be provided or multiple capacitance elements may be provided in parallel.

Figure 7:
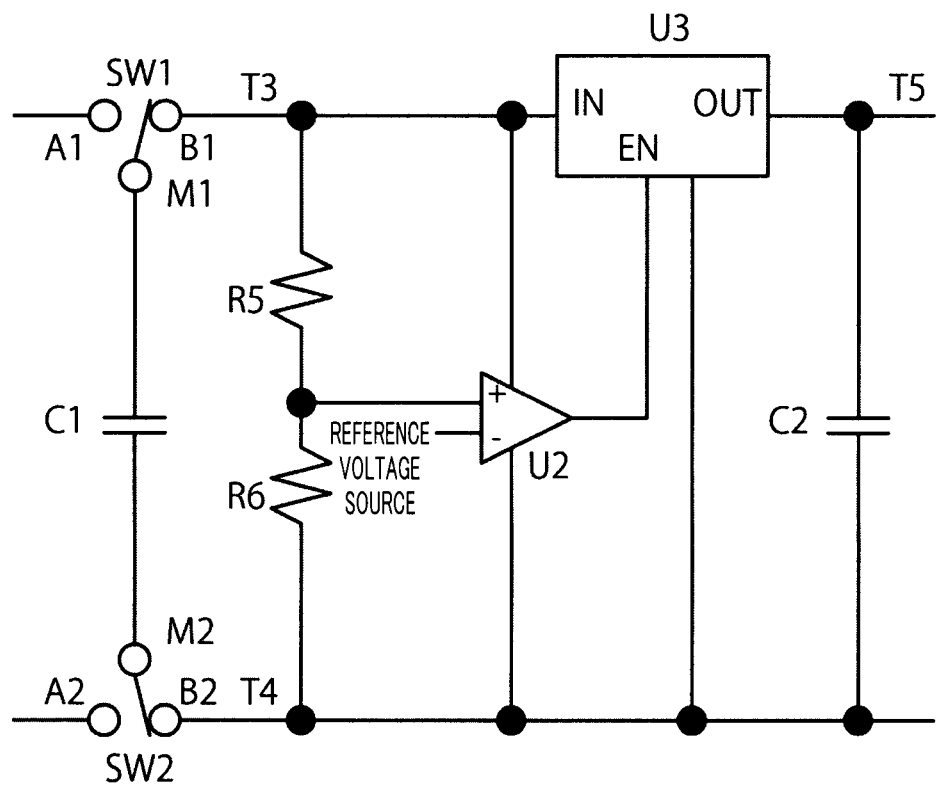
FIG. 7 is a diagram showing a modification on a measurement circuit side of the power supply circuit shown in FIG. 4.

A circuit configuration example on the electrocardiographic waveform measurement circuit 20 side of the power supply circuit 10 is explained. In FIG. 7, a modification on the electrocardiographic waveform measurement circuit 20 side of the circuit shown in FIG. 4 is shown.

When the capacitor is used as the power source as in this embodiment, an output voltage greatly fluctuates compared with when the secondary battery is used. Therefore, it is desirable to stabilize a voltage applied to the electrocardiographic waveform measurement circuit 20 and, when the output voltage is equal to or lower than a certain fixed voltage, to stop an electric current from flowing to the electrocardiographic waveform measurement circuit 20 to inhibit electric charges of the capacitor from uselessly decreasing.

To realize the configuration explained above, in the modification shown in FIG. 7, a comparator U2 is provided between the lead wires T3 and T4 on the electrocardiographic waveform measurement circuit 20 side of the capacitor C1. A reference voltage source is coupled to a minus terminal of the comparator U2. As the reference voltage source, a known circuit in which a reference voltage of approximately 1.2 V can be obtained called bandgap reference circuit is suitable in terms of safety. However, the reference voltage source is not always limited to the circuit and may be externally attached.

Resistors R5 and R6 are voltage dividing resistors coupled in series between the lead wires T3 and T4. Resistance values of the resistors R5 and R6 only have to be determined such that an electric current flowing through the resistors R5 and R6 has a sufficiently small value and, when the voltage of the lead wire T3 is an operation minimum voltage of the circuit, a midpoint voltage of the resistors R5 and R6 is the same as a reference voltage. The electric current flowing through the resistors R5 and R6 and a consumed current of the comparator U2 are negligibly small values compared with the consumed current of the electrocardiographic waveform measurement circuit 20.

The lead wire T3 is coupled to an input of a voltage regulator U3 including an enable (EN) terminal. An output of the comparator U2 is coupled to the EN terminal of the voltage regulator U3. A capacitor C2 is coupled between a lead wire T5, which is an output of the voltage regulator U3, and the lead wire T4. The capacitor C2 is added for circuit operation stabilization. The capacitor C2 can be omitted in some case.

The operation of the circuit shown in FIG. 7 is explained. When it is confirmed with a lighting state of the light emitting diode D1 shown in FIGS. 5 and 6 that the capacitor C1 is charged and the push button for operating the switches SW1 and SW2 is released, the switches SW1 and SW2 come into contact with the contacts B1 and B2. At this point in time, a terminal voltage of the capacitor C1 is higher than a voltage suitable for the operation of the electrocardiographic waveform measurement circuit 20 but is a proper voltage in the lead wire T5 on the output side of the capacitor C1 via the voltage regulator U3. An electric current is supplied to the electrocardiographic waveform measurement circuit 20 through the lead wire T5.

The terminal voltage of the capacitor C1 gradually decreases according to current consumption in the electrocardiographic waveform measurement circuit 20. When the terminal voltage is equal to or lower than the minimum operation voltage of the electrocardiographic waveform measurement circuit 20, the output voltage of the comparator U2 changes from H to L and the output of the voltage regulator U3 is stopped.

Thereafter, there is not current consumption in the electrocardiographic waveform measurement circuit 20. Therefore, the electric charges of the capacitor C1 are saved and a voltage drop of the capacitor C1 becomes extremely slow. Thereafter, the electric charges of the capacitor C1 are saved to a considerable degree. Therefore, a charging time at the time when the push button is pushed to bring the capacitor C1 into the charging state with the switches SW1 and SW2 during the next use can be set considerably short compared with an initial charging time.

Note that, in the above explanation, the EN terminal of the voltage regulator U3 is a positive logic. However, if the EN terminal is a negative logic, a plus terminal input and a minus terminal input of the comparator U2 only has to be reversed or an inverter only has to be added between the comparator U2 and the EN terminal of the voltage regulator U3.

In the power supply circuit 10 in this embodiment explained above, a supply source of electric power may be another information processing apparatus or the like or may be an independent power supply apparatus. In this embodiment, the ground side is set to the minus potential and the power supply side is set to the plus potential. However, the ground side and the power supply side may be set vice versa.

The voltage dividing circuit in this embodiment is the resistance voltage dividing circuit configured by the resistors R2 and R3 or the resistors R5 and R6. However, a system other than the resistance voltage division may be used if the voltage dividing circuit is a circuit that realizes the same function as a whole such as a diode or a current source circuit. The comparators U1 and U2 can be configured as appropriate as a general-purpose operational amplifier IC or a discrete circuit.

The voltage regulator U3 may be configured by a discrete circuit if an equivalent function is realized.

In this embodiment, the switches SW1 and SW2 are configured by the momentary-type DPDT switch of a spring return type. However, a switch of any principle and any structure may be adopted if the same function is realized.

With the power supply circuit 10 and the biological signal measuring apparatus including the power supply circuit 10 in this embodiment explained above, the measurement system and the power supply system are enabled to be electrically insulated with a simple configuration and a charging time can be greatly reduced to improve convenience.

Application examples of the power supply circuit 10 and the electrocardiographic waveform measurement circuit 20 in this embodiment are explained.

(1) Individual Authentication Using an Electrocardiographic Signal

The electrocardiographic waveform measuring apparatus including the power supply circuit of the present invention can be unitized and disposed on an operation surface of an apparatus requested to have strict security that is a target of individual authentication and use, for example, a safe or an important apparatus. To increase authentication accuracy, other authentication systems such as a password and fingerprint authentication can be concurrently used. It is hard to achieve completeness with any authentication method, for example, there is a risk of theft of the password and there is a possibility of duplication of the finger print by a malicious person. Therefore, multiple systems are often combined to increase the authentication accuracy. It is possible to easily increase authentication means if a unit including the electrocardiographic waveform measuring apparatus is used. The number of electrodes is two or three. In the case of two electrodes, the LEAD I is measured by one finger of the left hand and one finger of the right hand. In the case of three electrodes, as explained in the embodiment, it is suitable to enable another finger of the left or right hand to be placed on the third electrode and couple the third electrode to the ground or the DRL terminal. A time required for the authentication is usually several seconds to several ten seconds. Usually, measurement after the push button is pressed once for several seconds for charging is sufficient. If more time is required, a measurement time can be extended by pressing the push button again.

(2) Stress Check Using an Electrocardiographic Signal

It is known that a correlation between microscopic heart rate variability (HRV) and stress of a body is high and the stress is estimated to be larger as the HRV becomes smaller. Organizations such as companies are requested to appropriately manage stress of employees. In this connection, directly physically measuring a biological signal considered to represent a stress state is more advantageous than collecting data by means such as a questionnaire. In such a case, a form of renting out portable terminals is difficult to manage because there are risks of a loss of the terminal and a leak of acquired information such as data. Therefore, if the electrocardiographic waveform measuring apparatus is incorporated in a general-purpose apparatus such as a copying machine, an inhouse vending machine, a water heater, or a coffee server and a stress check can be easily performed at high frequency, stress management of members of an organization is easy. It is highly likely that stress of the organization as a whole decreases. The unit including this apparatus can be suitably applied to such a use. The number of electrodes and the measurement time extension can be realized in the same manner as (1).

Although the present disclosure has been described with reference to exemplary embodiments, those skilled in the art will recognize that various changes and modifications may be made in form and detail without departing from the scope of the claimed subject matter.

What is claimed is:

1. A power supply circuit that supplies electric power to a biological signal measurement circuit configured to detect, with an electrode set in contact with a human body, a biological signal which is a weak electric signal emitted by the human body, the power supply circuit comprising:
a capacitance element that accumulates the electric power; and
a circuit switch that is coupled between the capacitance element and an external power supply for supplying electric power to the capacitance element, and that is configured to switch, not through a state where the external power supply and the biological signal measurement circuit are electrically coupled, a first state where the capacitance element is made to establish electrical continuity with the external power supply and is enabled to be charged, and a second state where the capacitance element is made to establish electrical continuity with the biological signal measurement circuit and is enabled to supply power to the biological signal measurement circuit.

2. The power supply circuit according to claim 1, wherein the circuit switch is configured to retain the second state and come into the first state only for a period in which an external physical instruction is given.

3. The power supply circuit according to claim 2, wherein the circuit switch is a two-circuit two-contact push button switch of a momentary type.

4. The power supply circuit according to claim 1, wherein the capacitance element is an electric double layer capacitor.

5. The power supply circuit according to claim 1, further comprising a current detection circuit provided on an external power supply side of the circuit switch, the current detection circuit including a comparator, a voltage dividing resistor, a current detection resistor, and a light emitting diode, wherein
the power supply circuit lights up the light emitting diode when the capacitance element is charging and extinguishes the light emitting diode to perform a notification that the charging to the capacitance element is completed.

6. The power supply circuit according to claim 1, further comprising a voltage smoothing circuit provided on a biological signal measurement circuit side of the circuit switch, the voltage smoothing circuit including a comparator, a voltage dividing resistor, a reference voltage source, and a voltage regulator with an enable terminal, wherein
when an inter-terminal voltage of the capacitance element is equal to or lower than a minimum operation voltage of the biological signal measurement circuit, the power supply circuit stops the power supply to the biological signal measurement circuit to prevent a decrease in electric charges of the capacitance element.

7. A biological signal measuring apparatus comprising the power supply circuit according to claim 1.

* * * * *